United States Patent [19]

Willson

[11] Patent Number: 6,028,109
[45] Date of Patent: Feb. 22, 2000

[54] USE OF AGONISTS OF THE PEROXISOME PROLIFERATOR ACTIVATED RECEPTOR ALPHA FOR TREATING OBESITY

[75] Inventor: Timothy Mark Willson, Durham, N.C.

[73] Assignee: Glaxo Wellcome Inc., Research Triangle Park, N.C.

[21] Appl. No.: 09/155,321

[22] PCT Filed: Mar. 27, 1997

[86] PCT No.: PCT/EP97/01552

§ 371 Date: Sep. 25, 1998

§ 102(e) Date: Sep. 25, 1998

[87] PCT Pub. No.: WO97/36579

PCT Pub. Date: Oct. 9, 1997

[30] Foreign Application Priority Data

Mar. 30, 1996 [GB] United Kingdom .................. 9606805

[51] Int. Cl.[7] ................................................. A61K 31/195
[52] U.S. Cl. ........................................... 514/567; 514/909
[58] Field of Search ..................................... 514/567, 909

[56] References Cited

FOREIGN PATENT DOCUMENTS

| WO92 10468 | 6/1992 | WIPO . |
| WO95 18533 | 7/1995 | WIPO . |
| WO96 29405 | 9/1996 | WIPO . |

OTHER PUBLICATIONS

R. Mukherjee, et al., J. Steroid Biochem. Molec. Biol., vol. 51, No. ¾, 1994, pp. 157–166, "Human and Rat Peroxisome Proliferator Activated Receptors (PPARS) Demonstrate Similar Tissue Distribution But Different Responsiveness To PPAR Activators".

Keller, H., et al., Proceedings of The National Academy of Sciences of USA, vol. 90, No. 6, Mar.15,1993, pp. 2160–2164, "Fatty Acids and Retinoids Control Lipid Metabolism Through Activation of Peroxisome Proliferator–Activated Receptor–Retinoid X Receptor Heterodimers".

Kliewer, S.A., et al., Proceedings of the National Academy of Sciences of USA, vol. 91, Jul. 1994, pp. 7355–7359, "Differential Expression and Activation of a Family of Murine Peroxisome Proliferator–Activaed Receptors".

Forman, B.M., et al., Proceedings of the National Academy of Sciences, vol. 94, No. 9, Apr. 1997, pp. 4312–4317, Hypolipidemic Drugs, Polyunsaturated Fatty.

Assimacopoulos, F., et al., American Journal of Physiology, vol. 260, No. 2, 1991, pp. R278–R283, "Effects of A Peroxisome Proliferator on Beta–Oxidation and Overall Energy Balance in Obese (fa/fa) Rats".

*Primary Examiner*—Kimberly Jordan
*Attorney, Agent, or Firm*—Robert H. Brink

[57] ABSTRACT

The use of agonists of the peroxisome proliferator activated receptor alpha (PPARα) for the manufacture of a medicament for the treatment of obesity and methods of treating obesity comprising the administration of a therapeutic amount of a PPARα agonist.

6 Claims, No Drawings

USE OF AGONISTS OF THE PEROXISOME PROLIFERATOR ACTIVATED RECEPTOR ALPHA FOR TREATING OBESITY

This application is filed pursuant to 35 U.S.C. § 371 as a United States National Phase Application of International Application No. PCT/EP97/01552 filed Mar. 27, 1997, which claims priority from 9606805.1 filed Mar. 30, 1996.

The present invention is concerned with medicaments, and more particularly medicaments for use in the treatment of obesity.

Obesity can be described as a state of excessive accumulation of body fat, and is widely considered to be a major public health problem, being associated with substantially increased morbidity and mortality, as well as psychological problems, reduced economic achievement, and discrimination. Examples of health and social problems thought to be caused or exacerbated by obesity include coronary heart disease, stroke, obstructive sleep apnoea, diabetes mellitus, gout, hyperlipidemia, osteoarthritis, reduced fertility, impaired psychosocial function, reduced physical agility and increased risk of accidents, impaired obstetrical performance, reduced economic performance and discrimination and prejudice.

Causes of obesity remain unclear, however whether obesity is of genetic origin or is promoted by a genotype-environment interaction, or both, it remains true that energy intake must have exceeded metabolic and physical (work) energy expenditure for there to have been surplus energy available for fat deposition. There remains considerable uncertainty, however, over the relative importance of different mechanisms in achieving this positive energy balance.

Treatment of obesity remains a problem. Although it is well established that morbidity and mortality are increased in obese individuals, it is unclear whether dieting results in decreased long-term risk of early death. The major obesity intervention has been the many different forms of dieting, which are often fads without a sound scientific basis. Results have shown that dieting is a component of the weight loss regimens of 84% of women and 76–78% of men attempting to lose weight. A further important obesity intervention is physical activity which increases energy expenditure, both during the actual period of exercise and during subsequent period of rest. Thus, exercise can promote negative energy balance provided that energy intake is not increased concomitantly. Exercise, however, in general, has been found to be only moderately successful in promoting weight loss. A program combining both dieting and exercise as well as behaviour modification is widely viewed as the optimal approach to weight loss. Food restriction alone can be very successful in promoting weight loss, but, a significant component of the weight loss can be lean tissue. In addition, food restriction results in a decline in total energy expenditure which serves to reduce the extent of negative energy balance. Studies have demonstrated that combination programs involving both food restriction and exercise promote a substantial loss of fat and, at the same time, promote a maintenance of lean tissue.

It can be appreciated from the above that obesity remains a problem, and that no reliable treatment thereof has been established. There is therefore a need to develop medicaments and treatment regimes effective in the alleviation of obesity. We have now unexpectedly found that a certain group of compounds are particularly advantageous for use in the treatment of obesity.

More particularly we have found that agonists of the peroxisome proliferator activated receptor alpha (hereinafter referred to as PPARα) are useful in the treatment of obesity. Peroxisome proliferator activated receptor (hereinafter referred to as PPAR) is a known member of the steroid/retinoid/thyroid hormone receptor family of ligand activated transcription factors and is activated, interalia, by high micromolar concentrations of certain peroxisome proliferators. PPARα, peroxisome proliferator activated receptor gamma (hereinafter referred to as PPARγ) and peroxisome proliferator activated receptor delta (hereinafter referred to as PPARδ or NUCI) have respectively been identified as subtypes of PPARs.

The present invention therefore provides PPARα agonists for use in the treatment of obesity, and methods of treating obesity employing PPARα agonists. More particularly, the present invention provides the use of potent and selective PPARα agonists for use in the treatment of obesity. For example, we have found that a potent and selective PPARα agonist represented by formula (I) (or a pharmaceutically acceptable salt thereof) is useful in the treatment of obesity:

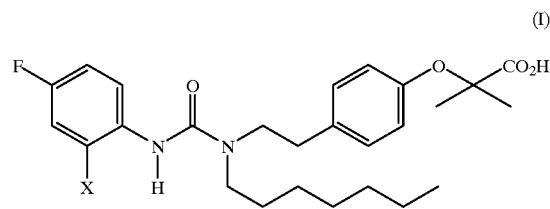

wherein X represents hydrogen or fluorine.

A compound of formula (I) wherein X represents fluorine is specifically disclosed in Example 3 of WO92/10468. However, there is no disclosure or suggestion in WO92/10468 of obesity treatment.

Reference to a compound of formula (I) as used herein includes reference to pharmaceutically acceptable salts thereof, a particularly apt salt being N-methyl-glucamine.

References hereinafter to a compound of formula (I) includes the compound and its pharmaceutically acceptable salts.

The following are particular aspects of the present invention:
 (a) a PPARα agonist (e.g. a compound of formula (I)) for use as a therapeutic agent in the treatment of obesity;
 (b) pharmaceutical formulations comprising a PPARα agonist (e.g. a compound of formula (I)) and at least one pharmaceutical carrier, wherein the PPARα agonist is present in an amount effective for use in the treatment of obesity;
 (c) the use of a PPARα agonist (e.g. a compound of formula (i)) in the manufacture of a medicament for the treatment of obesity;
 (d) a method of treating obesity in a mammal, such as a human, which comprises the administration of a therapeutically effective amount of a PPARα agonist (e.g. a compound of formula (I)) to a said mammal.

The term 'treatment' as used herein includes prophylaxis as well as alleviation of established obesity. In addition to the treatment of obesity, a method according to the present invention has application in the treatment of conditions associated with obesity, such as coronary heart disease, stroke, obstructive sleep apnoea, diabetes mellitus, gout, hyperlipidemia, osteoarthritis, reduced fertility, impaired psychosocial function, reduced physical agility and increased risk of accidents, impaired obstetrical performance, reduced economic performance and discrimination and prejudice as herein before described.

A recognised clinical and epidemiological measure for the classification of obesity is the Body Mass Index (BMI) which is defined as weight in kilograms divided by the square of height in meters. Typically, a BMI of 25–30 is considered as overweight and >30 as obese. Treatment according to the present invention generally refers to a lowering of BMI to less than about 29 to 31. It will however be appreciated by persons skilled in the art that obesity is inherently difficult to classify, and that the cut-off point for the definition of obesity is necessarily arbitrary, in part because body fatness is a continuum. However, in general terms treatment according to the present invention desirably prevents or alleviates obesity to an extent whereby there is no longer a significant health risk to the patient.

The amount of a PPARα agonist which is required to achieve the desired biological effect will, of course, depend on a number of factors, for example, the mode of administration and the precise clinical condition of the recipient. In general, the daily dose will be in the range of 0.1 mg–1 g/kg, typically 0.1–100 mg/kg. An intravenous dose may, forexample, be in the range of 0.01 mg to 0.1 g/kg, typically 0.01 mg to 10 mg/kg, which may conveniently be administered as an infusion of from 0.1 $\mu$g to 1 mg, per minute. Infusion fluids suitable for this purpose may contain, for example, from 0.01 $\mu$g to 0.1 mg, per millilitre. Unit doses may contain, for example, from 0.01 $\mu$g to 1 g of a PPARα agonist. Thus ampoules for injection may contain, for example, from 0.01 $\mu$g to 0.1 g and orally administrable unit dose formulations, such as tablets or capsules, may contain, for example, from 0.1 mg to 1 g.

A PPARα agonist may be employed in the treatment of obesity as the compound per se, but is preferably presented with an acceptable carrier in the form of a pharmaceutical formulation. The carrier must, of course, be acceptable in the sense of being compatible with the other ingredients of the formulation and must not be deleterious to the recipient. The carrier may be a solid or a liquid, or both, and is preferably formulated with the agonist as a unit-dose formulation, for example, a tablet, which may contain from 0.05% to 95% by weight of the agonist.

The formulations include those suitable for oral, rectal, topical, buccal (e.g. sub-lingual) and parenteral (e.g. subcutaneous, intramuscular, intradermal or intravenous) administration.

Formulations suitable for oral administration may be presented in discrete units, such as capsules, cachets, lozenges or tablets, each containing a predetermined amount of a PPARα agonist; as a powder or granules; as a solution or a suspension in an aqueous or non-aqueous liquid; or as an oil-in-water or water-in-oil emulsion. In general, the formulations are prepared by uniformly and intimately admixing the active PPARα agonist with a liquid or finely divided solid carrier, or both, and then, if necessary, shaping the product. For example, a tablet may be prepared by compressing or moulding a powder or granules of the PPARα agonist optionally with one or more accessory ingredients. Compressed tablets may be prepared by compressing, in a suitable machine, the compound in a free-flowing form, such as a powder or granules optionally mixed with a binder, lubricant, inert diluent and/or surface active/dispersing agent (s). Moulded tablets may be made by moulding, in a suitable machine, the powdered compound moistened with an inert liquid diluent.

Formulations suitable for buccal (sub-lingual) administration include lozenges comprising a PPARα agonist in a flavoured base, usually sucrose and acacia or tragacanth, and pastilles comprising the agonist in an inert base such as gelatin and glycerin or sucrose and acacia.

Formulations of the present invention suitable for parenteral administration conveniently comprise sterile aqueous preparations of a PPARα agonist, preferably isotonic with the blood of the intended recipient. These preparations are preferably administered intravenously, although administration may also be effected by means of subcutaneous, intramuscular, or intradermal injection. Such preparations may conveniently be prepared by admixing the agonist with water and rendering the resulting solution sterile and isotonic with the blood. Injectable compositions according to the invention will generally contain from 0.1 to 5% w/w of the agonist.

Formulations suitable for rectal administration are preferably presented as unit-dose suppositories. These may be prepared by admixing a PPARα agonist with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include vaseline, lanolin, polyethylene glycols, alcohols, and combinations of two or more thereof. The PPARα agonist is generally present at a concentration of from 0.1 to 15% w/w of the composition, for example, from 0.5 to 2%.

A compound of formula (I) may be prepared as described in Example 3 of WO92/1 0468.

The present invention will now be further illustrated by the by the aacompanying Examples which do not limit the scope of the invention in any way.

EXAMPLE 1

2-(4[2-(3-[4-fluorophenyl]-1-heptylureido)ethyl]-phenoxy)-2-methylpropionic acid (Compound of formula (I), where X=H)

1.6 g of 4-fluorophenyl isocyanate was added to a solution of 3.3 g of ethyl 2-[4-(heptylaminoehtly)phenoxy]-2-methylpropionate [WO 92/10468, example 2, intermediate (d)] in 50 mL of $CH_2Cl_2$. The resulting solution was stirred at room temperature for 18 hours and then concentrated in vacuo. The residue was purified by flash chromatography ($Si_2O$, 2:1:1 hexane/$CH_2Cl_2$/ethyl acetate) to yield 4.8 g of ethyl 2-(4{-2-[3-(4-fluorophenyl)-1-heptylureido]ethyl}phenoxy)-2-methylpropionate as a light brown oil.

2.4 g of ethyl 2-(4-[2-(3-[4-fluorophenyl]-1-heptylureido)ethyl]phenoxy)-2-methylpropionate was dissolved in 50 mL of ethanol and 30 mL of 1N aqueous sodium hydroxide was added. The resulting solution was heated at reflux for 30 minutes, cooled to room temperature, acidified with 100 ml of 2N aqueous HCl and extracted with CH2Cl$_2$. The organic extract was washed with water and brine, dried over magnesium sulfate and concentrated in vacuo. The resulting solid was recrystalized from diethyl ether/hexane to yield 1.1 g of the title compound as a white powder; m.p. 162–4° C.; $^1$H NMR ($CD_3OD$, δ, 300 MHz): 7.35-6.7 (7H, m, aromatic), 3.48 (2H, t, $NCH_2$), 3.24 (2H, t, $NCH_2$), 2.76 (2H, t, $ArCH_2$), 1.5-1.1 (10H, m, $(CH_2)_5CH_3$), 1.45 (6H, s, $(CH_3)_2C$), 0.83 (3H, t, $(CH_2)_5CH_3$).

EXAMPLE 2

Radioligand [$^3$H]-2-(4-[2-(3-[4-fluorophenyl]-1-heptylureido)-ethyl]phenoxy)-2-methylpropionic acid 1.2 g of ethyl 2-[4-(2-aminoethyl)phenoxy]-2-methylpropionate [WO 92/10468, example 2, intermediate (c)] was dissolved in THF (20 mL). Hept6-enal (0.43 g) and 4A sieves (0.6 g) were added. After 10 minutes, 0.25 g of sodium cyanoborohydride was added and the mixture stirred at room temperature for 50 minutes. The reaction mixture was poured into 5% aq. sodium carbonate and extracted with ethyl acetate. The organic extract was washed with brine, dried over $MgSO_4$ and concentrated. Purification by flash chromatography (5–10% $MeOH/CH_2Cl_2$) gave 0.15 g of ethyl 2-[4-(2-amino-[6-heptenyl]ethyl) phenoxy]-2-methylpropionate as a light brown viscous oil. This material was dissolved in $CH_2Cl_2$ (5 mL) and 4-fluorophenylisocyanate (0.05 mL) was added. The solution was stirred at rt for 3 hours and then concentrated. Purification by flash chromatography gave 0.08 g of ethyl 2-(4-[2-(3-[4-fluorophenyl]-1-[6-heptenyl]ureido) ethyl] phenoxy)-2-methylpropionate as a yellow solid. This material was dissolved in EtOH (3 mL) and 1M aq. NaOH (1.5 mL), and the solution was heated at reflux for 30 min. The solution was concentrated, poured into 1N HCl and extracted with EtOAc, washed with brine, dried over $MgSO_4$, and concentrated to a yellow solid. Recrystallization fron ether/hexane gave 0.05 g of 2-(4-[2-(3-[4-fluorophenyl]-1-[6-heptenyl]ureido)ethyl]phenoxy)-2-methylpropionic acid as a white powder; m.p. 143–5 degC.

A solution of 2-(4-[2-(3-[4-fluorophenyl]-1-[6-heptenyl] ureido)ethyl]phenoxy)-2-methylpropionic acid (10 mg) in anhydrous DMF (3.5 mL) was transferred to a reaction vessel containing 10% Pd/C (9.8 mg). The reaction vessel was evacuated and degassed via one freeze-thaw-evacuation cycle and then exposed to tritium gas (10.1 Ci). The reaction was terminated after 4.3 hours and the catalyst was removed by filtration through a short column of celite. The catalyst was further washed with ethyl acetate (3 mL) and methanol (2 mL). The solvents were removed in vacuo and any labile tritium was removed by evaporation with methanol (4×mL) The residue was dissolved in acetonitrile (20 mL) and filtered to a provide a solution of the labeled compound (33.3 mCi/mL,1863 mCi). HPLC analysis (Dynamax C8, 20 min gradient from 4:6 ACN:0.1% TFA to 9:1 ACN:0.1% TFA, 254 nm, on-line radioactivity detection with Berthold flow monitor,retention time, 22.4 min) of the solution indicated a radiochemical purity of 80%. A portion of this solution (0.8 mL, 26.6 mCi) was purified by HPLC (Dynamax C8, 25 min gradienet from 4:1 AcN:0.1% TFA to 9:1 ACN: 0.1% TFA, 235 nm). Fractions containg pure material were combined and evaporated under nitrogen. The residue was redissolved in acetonitrile to provide a solution of the title compound (9.38 mCi, 1.817 mCi/mL, specific activity, 83.8 Ci/mmol, radiochemical purity, 98.9%).

EXAMPLE 3

Binding Data a) Binding of the radioligand of Example 2 to PPARα The ligand binding domains of mouse and human PPARα were expressed in *E. Coli* as fusion proteins with glutathione-S-transferase (GST). DNA encoding the ligand binding domain of mouse and human PPARa was amplified via polymerase chain reaction and inserted in-frame into the bacterial expression vector pGEX-2T (Pharmacia). GST-mPPARα and GST-hPPARa fusion proteins were expressed in BL21(DE3)plysS cells. After a 2 hour induction with 1 mM IPTG, the cells were lysed by freeze/thaw in 1/10 volumes of a buffer containing 50 mM Tris (pH 8), 250 mM KCl, 10 mM DTT, 1 mM PMSF, and 1% Triton X-100. Lysates were clarified by centrifugation for 1 hr at 50,000 x g. 1.5 ml of a 50% glutathione-sepharose bead (Pharmacia)/phosphate buffered saline slurry was added to 10 ml of clarified lysate, the mixture incubated for 30 minutes, and the glutathione-sepharose bead-GST-PPARα complexes were then collected by centrifugation and washed twice in binding buffer containing 50 mM KCl, 10 mM Tris (pH 8), 1 mM DTT. The washed glutathione-sepharose bead-PPARα complexes were resuspended in 0.75 ml binding buffer containing 10% glycerol.

For binding reactions, 10-20 microliter of the glutathione-sepharose bead-PPARα slurry was incubated at 4 degrees celsius for 2 hours in binding buffer (final volume=100 microliter) with the radioligand of Example 2 in the presence or absence of a 100-fold excess of the title compound of Example 1 (hereinafter referred to as Compound A). The glutathione-sepharose bead-GST-PPARα complexes were collected by centrifugation and washed twice in binding buffer. The glutathione-sepharose bead-GST-PPARα complexes were then resuspended in scintillation fluid and the tritium quantitated by liquid scintillation counting.

Binding affinity analyses were done by varying the concentration of the radioligand of Example 2 from 7.5 nM to 200 nM. Specific, saturable binding of Compound A was observed in experiments in which either the mouse or human PPARα-GST fusion protein was used, Kd=100 nM.

b) Competition binding of the Compound A, and 2-(4-[2-(3-[2,4-difluorophenyl]-1-heptylureido) ethyl]-phenoxy)-2-methylpropionic acid (Compound of formula (I), where X=F, hereinafter referred to as Compound B) for PPARα For competition binding reactions, 10-20 microliter of the glutathione-sepharose bead-PPARα slurry was incubated at 4 degrees celsius for 2 hours in binding buffer (final volume=100 microliter) with 100 nM of the radioligand of Example 2 in the presence or absence of a 1000-fold excess (100 microM) of Compound A or Compound B. The glutathione-sepharose bead-GST-PPARα complexes were collected by centrifugation and washed twice in binding buffer. The glutathione-sepharose bead-GST-PPARα complexes were then resuspended in scintillation fluid and tho tritium quantitated by liquid scintillation counting.

| No competitor | 40,200 cpm bound |
| Compound A | 18,300 cpm bound |
| Compound B | 13,000 cpm bound |

EXAMPLE 4

A transient cotransfection assay was used to screen for PPARα activator activity of compounds of formula (I).

As mammalian cell lines contain endogenous nuclear receptors that can complicate interpretation of the results, we used an established chimera system in which the ligand-binding domain of the PPAR-α was fused to the DNA binding domain of the yeast transcription factor GAL4.The GAL4-PPARα chimera was cotransfected into CV-1 cells with a reporter construct containing five copies of the GAL4 binding site upstream of the thymidine kinase promotor driving secreted placental alkaline phosphatase (SPAP) as reporter.

Plasmids

GAL4-PPAR chimera and UAS-tk-CAT/SPAP reporters. The GAL4-PPAR expression constructs contain the translation initiation sequence and amino acids 1-76 of the human glucocorticoid receptor fused to a nucleotide sequence encoding for amino acids 1-147 of GAL4 in the pSG5 expression vector (Stratagene). A nucleotide sequence encoding for amino acids 174–475 of PPARα, as amplified =by polymerase chain reaction (PCR) using vent polymerase (New England Biolabs) and inserted C-terminal to the GAL4 sequences. The UAS-tk-CAT/SPAP reporter contains 5 copies of the GAL4 binding site inserted into pBLCAT2 or pG12-tk-SPAP (Luckow, B et al, 1987 and Berger et al, 1988) pSG-PPAR. Nucleotide sequences encoding for PPARα were inserted into the expression vector pSG5 (Stratagene).

aP2-tk-CAT. The 518 bp EcoR1/Xba1 fragment containing the enhancer of the aP2 gene (Graves et al., 1992) was inserted into pBLCAT2 (Luckow and Schutz, 1987).

Transfection assay; SPAP reporter. CV-1 cells were plated in DME medium supplemented with 10% delipidated fetal calf serum at a density of $2.4 \times 10^4$ cells per well in a 96-well plate (Costar) 16–24 h before transfection. In general, 8.0 ng of reporter plasmid, 25.0 ng of β-galacotosidase expression vector (pCH110, Pharamacia), and 2.0 ng of GAL4-PPARα expression vector were mixed with carrier DNA (pBluescript, Stratagene) to a total of 80 ng of DNA per well in a volume of 10 μl optiME medium (GIBCO BRL). To this, a second mix, containing 9.3 μl optiME medium (GIBCO BRL) and 0.7 μl of LIPOFECTAMINE™ (GIBCO BRL), was added. After 30 min; an additional 80 μl of optiME medium were added and the combined mix was then applied to the cells. 16 h later the medium was exchanged to DME medium supplemented with 10% delipidated fetal calf serum and the test compound at a concentration of $10^{-5}$M. After incubation for an additional 24 h SPAP activity and β-galactosidase activity were measured as previously described (Pfahl et al., 1990).

Transfection assay: CAT reporter. CV-1 cells were plated in DME medium supplemented with 10% delipidated fetal calf serum at a density of $1.2 \times 10^5$ cells per well in a 24-well plate (Costar) 16–24 h before transfection. In general, 100 ng of reporter plasmid, 200 ng of β-galactosidase expression vector (pCH110 Pharamacia), and variable amounts of receptor expression vector were mixed with carrier DNA (pBluescript, Stratagene) to 500 ng of total DNA per well in a volume of 50 μl optiME medium (GIBCO BRL). To this mix, 50 μl of a 1:10 dilution of LIPOFECTAMINE™ (GIBCO BRL) in optiME medium was added. After 30 min an additional 400 μl of optiME medium was added and the total mix applied to the cells. 16 h later, the medium was exchanged to DME medium supplemented with 10% delipidated fetal calf serum and the test compound at the indicated concentration. After incubation for an additional 24 h, chloramphenicol acetyl transferase (CAT) activity and β-galactosidase activity were measured as previously described (Pfahl et al., 1990). CAT activity was normalized for transfection effeciency by using the cotransfected β-galactosidase expression plasmid (pCH110, Pharmacia) as internal standard.

The following EC50 values were obtained for compounds of formula (I) employing the transfection assay.

| Formula (I) | mPPARαEC5O (nM) | hPPARαEC5O (nM) |
|---|---|---|
| X = Fluorine | 25 | 720 |
| X = Hydrogen | 13 | 545 |

EXAMPLE 5

Male Golden Syrian hamsters (supplied by Charles River), weighing approximately 140–150 g at the start of the study, were subjected to the following dietary regime. On day 0, four groups of animals (n=6/group) were begun on a diet consisting of rodent chow containing 1% cholesterol. Three of the four groups on the cholesterol diet also began oral dosing with Compound A as described in Example 3 (0.05, 0.1, 0.25 and 0.5 mg/kg/day). Compound A was given as a suspension in 5% bicarbonate and 0.5% methyicellulose. The study was carried out for 14 days.

The above dietary regime was also carried out with Compound B, but the dosages of Compound B employed were 0.1, 0.5 and 1mglkg/day.

The changes of body weight observed were as follows:

Compound A Test
1. Chow containing 1% cholesterol—gained 23.2 g
2. Chow containing 1% cholesterol, plus 0.05 mg/kg of Compound A—gained 20 g.
3. Chow containing 1% cholesterol, plus 0.1 mg/kg of Compound A—gained 26.2 g.
4. Chow containing 1% cholesterol, plus 0.25 mg/kg of Compound A—gained 12.6 g.
5. Chow containing 1% cholesterol, plus 0.5 mg/kg of Compound A—gained 3.4 g.

Compound B Test
1. Chow containing 1% cholesterol—gained 13 g;
2. Chow containing 1% cholesterol, plus 0.1 mg/kg of Compound B—gained 1 1 g;
3. Chow containing 1% cholesterol, plus 0.5 mglkg of Compound B—lost 12.3 g;
4. Chow containing 1% cholesterol, plus 1 mg/kg of Compound B—lost 12.4 g.

I claim:

1. A method of treatment of obesity in a mammal which comprises the administration of a therapeutically effective amount of a PPARα agonist to said mammal.

2. The method of claim 1 wherein said agonist is selective for PPARα.

3. The method of claim 1 wherein said agonist is a compound of formula (I)

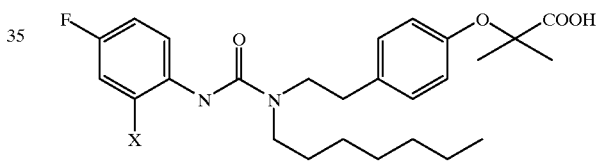

(I)

wherein X is H or F, or a pharmaceutically acceptable salt thereof.

4. The method of claim 1 wherein said agonist is

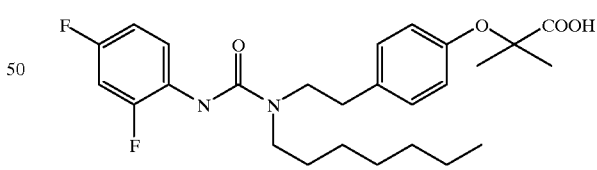

(I)

or a pharmaceutically acceptable salt thereof.

5. A method of treatment of obesity in a mammal which comprises the administration of a pharmaceutical formulation comprising a therapeutically effective amount of a PPARα agonist.

6. The method of claim 5 wherein said formulation further comprises a pharmaceutically acceptable carrier.

* * * * *